United States Patent [19]

Paudler et al.

[11] 4,105,434

[45] Aug. 8, 1978

[54] HERBICIDAL 5,5'-BIS-1,2,4-TRIAZINYLS

[75] Inventors: William W. Paudler, Tuscaloosa, Ala.; Robert E. Moser, Mentor; Norman M. Pollack, University Heights, both of Ohio

[73] Assignee: Diamond Shamrock Corporation, Cleveland, Ohio

[21] Appl. No.: 760,033

[22] Filed: Jan. 17, 1977

[51] Int. Cl.² .................. C07D 253/06; A01N 9/22
[52] U.S. Cl. ........................................ 71/93; 544/182
[58] Field of Search .................. 260/240 AS, 249.5; 71/93; 544/182

[56] References Cited

U.S. PATENT DOCUMENTS 3,498,981 3/1970 Culbertson .................. 544/182

OTHER PUBLICATIONS

Krass et al., J. Het. Chem., vol. 10, pp. 343–345, (1973).
Krass et al., J. Het. Chem., vol. 11, pp. 43–44, (1974).

*Primary Examiner*—John M. Ford
*Attorney, Agent, or Firm*—Stuart L. Melton

[57] ABSTRACT

Herbicidally active 5,5'-bis-1,2,4-triazinyl compounds, compositions and methods of using same to control undesired vegetation.

21 Claims, No Drawings

HERBICIDAL 5,5'-BIS-1,2,4-TRIAZINYLS

BACKGROUND OF THE INVENTION

The present invention relates to unsubstituted, monosubstituted and disubstituted 5,5'-bis-1,2,4-triazinyl compounds which possess valuable herbicidal activity, particularly as selective herbicides for agronomic crops such as corn, sorghum, soybeans, wheat, oats and the like. The instant invention further relates to active herbicidal compositions and to methods for controlling inhibiting or modifying the growth of vegetation.

Various 1,3,5-triazine compounds have been previously suggested for use in the control of undesired weeds (see, for example, Belgian Pat. No. 549,590). Moreover, various structurally unrelated bis-1,2,4-triazinyl compounds have been suggested as a potentially active class of fungicides and herbicides (see, for example, U.S. Pat. No. 3,498,981).

The preparation of certain substituted bis-1,2,4-triazinyl compounds are described in Krass et al. "1,2,4-triazines X: Dimerizations of 1,2,4-triazines" in J. Hetero. Chem., Vol. 10, 343 (1973) and Krass et al., "1,2,4-triazines XII: Synthesis of 5-carboxamido-1,2,4-triazines via an Addition-Oxidation Reaction", J. Hetero. Chem. Vol. 11, 43–44 (1974)). More specifically, these authors have described the preparation of 5,5'-bis-1,2,4-triazinyls by sodium methoxide or aqueous potassium cyanide catalyzed coupling of suitable triazine starting materials.

U.S. Pat. No. 3,498,981 to Culbertson, granted Mar. 3, 1970, describes various 5-monosubstituted-3,5-disubstituted-3,3'-bis- and 5,5'-bis- as-triazinyls and methods for the preparation thereof. The substituents at the 3,3' positions of the respective triazine rings include alkyl, carbocyclic aromatic, pyridyl, pyrimidyl, quinolyl and thiazolyl of 1 to 20 carbon atoms. The preferred exemplified compounds have substituted aromatic carbocyclic or nitrogen-containing heterocyclic substituents at the 3,3' positions as well as at the 5,5' positions. The patentee indicates that the compounds and compositions of the invention are useful as corrosion inhibitors for lubricating oils, coatings for metal substrates and to provide a sensitive test for the presence of ferrous ions and that bis-as-triazinyls containing ferroin moieties may be useful as fungicides or herbicides (although no specific test data with respect to herbicidal activity is presented).

U.S. Pat. No. 3,671,523, granted June 20, 1972, relates to various substituted 4-amino-1,2,4-triazine-5-one herbicidal agents outside the scope of the instant bis-1,2,4-triazinyls.

SUMMARY OF THE INVENTION

It is, therefore, a primary object of the present invention to provide herbicidally active unsubstituted and substituted 5,5'-bis-asymmetric 1,2,4-triazinyls.

Another object of the invention is to provide methods of using such bis-asymmetric triazinyls as pre-emergence and post-emergence herbicides and phytotoxicants.

A still further object of the present invention is to afford certain novel bis-asymmetric triazinyl compounds for use as herbicides.

An additional object of the present invention is to afford herbicidally effective formulations or compositions of the active bis-asymmetric triazinyl compounds of the invention or admixtures thereof with other known herbicides, optionally further combined with suitable inert liquid or solid carriers, vehicles or adjuvants in the form of solutions, emulsions, suspensions, emulsifiable concentrates, spray powders, pastes, soluble powders, dusting agents, granulates and the like.

These and other similar objects, advantages and features are accomplished according to the methods, products and compositions of the invention wherein bis-1,2,4-triazinyls are advantageously employed pre-emergence and, particularly, post-emergence for the selective control of undesirable broadleaf weeds and grasses.

DESCRIPTION OF THE PREFERRED EMBODIMENTS

It has now been found that 5,5'-bis asymmetric triazinyls of the general formula

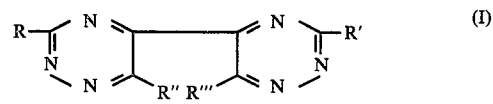

wherein R and R' are the same or different and represent hydrogen, alkyl (e.g. $C_1$–$C_6$, and preferably, $C_1$–$C_4$ alkyl), alkoxy (e.g. $C_1$–$C_6$, and preferably, $C_1$–$C_4$ alkoxy), alkylamino ($C_1$–$C_4$ alkyl), dialkylamino, (e.g., $C_1$–$C_4$ alkyl), alkylsulfonyl (e.g., $C_1$–$C_4$ alkyl), azido, alkylthio (e.g., $C_1$–$C_4$ alkyl), or a group —OA wherein A is a cation (e.g. alkali metal, preferably sodium or potassium), and R″ and R‴ are the same or different and represent hydrogen or alkyl (e.g. $C_1$–$C_4$ alkyl) with the alkyl moieties of R, R', R″ and R‴ being branched or straight chain and the 1,1'-N-oxide derivatives of the foregoing and mixtures of the foregoing compounds possess valuable herbicidal activity, particularly as selective herbicides for the post-emergent control of broadleaf weeds and grasses in agronomic crops such as corn, grain, sorghum, soybeans, oats and, especially, wheat.

As specifically preferred compounds of the aforementioned general formula, for use as herbicides, there may be mentioned 5,5'-bis-1,2,4-triazinyl, 3,3'-dimethylthio-5,5'-bis-1,2,4-triazinyl, 3,3'-dimethoxy-5,5'-bis-1,2,4-triazinyl, 3,3'-diethoxy-5,5'-bis-1,2,4-triazinyl, 3,3'-dipropoxy-5,5'-bis-1,2,4-triazinyl, 3,3'-dibutoxy-5,5'-bis-1,2,4-triazinyl, 3,3'-dimethyl-5,5'-bis-1,2,4-triazinyl, 3,3'-diethyl-5,5'-bis-1,2,4-triazinyl, 3,3'-dimethylthio-6,6'-dimethyl-5,5'-bis-1,2,4-triazinyl, 3,3'-diazido-5,5'-bis-1,2,4-triazinyl, 3,3'-dimethylamino-5,5'-bis-1,2,4-triazinyl, 3,3'-di-(dimethylamino)-5,5'-bis-1,2,4-triazinyl, 1,1'-di-N-oxide-3,3'-dimethylamino (or dimethoxy)-5,5'-bis-1,2,4-triazinyl, 3,3'-di-methylsulfonyl-5,5'-bis-1,2,4-triazinyl, 3,3'-dibutyl-5,5'bis-1,2,4-triazinyl, 3,3-dihydroxy-5,5'-bis-1,2,4-triazinyl (dipotassium salt) and 3-methylthio, 3'-methoxy-5,5'-bis-1,2,4-triazinyl.

While certain of the bis-1,2,4-triazinyl compounds set forth hereinabove in formula (I) useable in accordance with the practices of the present invention have heretofore been described (cf. J. Hetero. Chem., Vol. 10, 343, 1973), the following compounds of the general formula (I) are novel herbicidally active compounds wherein correspondingly R and R' are the same and selected from n-butyl, propoxy, butoxy, azido ($N_3$), hydroxide (alkali metal salt), methylamino, dimethylamino or methylsulfonyl and R″ and R‴ are each hydrogen; or wherein R and R' are different and independently selected from methylthio and methoxy and R″ and R‴ are each hydrogen; or wherein R and R' are the same and selected from dimethylamino or dimethoxy, R" and R''' are each hydrogen and the 1,1'-hetero nitrogen atoms are substituted by oxygen to form the N-oxides.

The compounds of the present invention may be simply prepared by following the coupling or condensation procedures outlined in the aforementioned literature articles with appropriate selection of the alkyl, alkoxy, alkylthio, azide, alkylsulfonyl, etc. substituted or disubstituted triazine starting material to obtain the desired 5,5-bis-asymmetric triazinyl compounds of the invention. The N-oxide derivatives may be prepared by conventional methods. Likewise, the metal salts can be made conventionally. In addition to the foregoing synthesis methods and the procedures set forth in the examples hereinbelow, it may also be advantageous to utilize, for instance, the oxamide dihydrazone reaction sequence set forth in Examples 5 and 6 of U.S. Pat. No. 3,498,981 with appropriate selection of a substituted glyoxal reactant to obtain the desired product in accordance with the present invention.

The present invention specifically contemplates methods of selectively controlling or combating undesired plant systems, e.g., broadleaf weeds and grasses comprising applying to the undesired plants directly or to the soil surface, or plant locus or situs a herbicidally effective amount of an active compound of the invention alone or in combination with a preselected carrier, vehicle or adjuvant. These herbicidal compositions may be applied in the conventional manner, for example, by spraying, atomizing, scattering, dusting, sprinkling, etc. Moreover, the compounds, compositions and formulations of the invention may be applied pre-emergent to the soil surface or post-emergent to the foliage of the plant systems.

As noted previously, the 5,5'-bis-asymmetrical triazinyls employed as effective herbicides herein, display acceptable selectivity toward various crops including corn, soybeans, grain sorghum, and the like and, specifically, display excellent selectivity with respect to wheat. Therefore, in accordance with one of the preferred embodiments of the invention, the bis-asymmetrical triazinyl compounds of the invention are utilized as selective herbicides for the post-emergent control of broadleaf weeds and grasses in wheat.

As employed herein, the expression "selective herbicidal compounds or compositions" is intended to mean that the compounds and compositions thereof in accordance with the present invention when simultaneously applied to an undesired plant species and the desired crop, selectively impair or inhibit the growth of or destroy the undesired plant systems without adversely affecting the normal growth and development of the crop. Thus, when applied at a dosage rate ranging between about 0.015 pounds per acre (lb/A) to about one pound per acre, and preferably about 0.031 to 0.5 lb/A, and most preferably 0.062 to 0.25 lb/A the herbicidally active compounds employed herein function as selective herbicides for certain crops.

It is further contemplated, however, that the herbicidal compositions of the present invention may be applied at higher dosage rates with respect to the active compound to obtain a total or complete herbicidal effect. As used herein, the expression "total or complete herbicide or herbicidal composition" is intended to mean that no crop selectivity is observed and all plant species (undesired weeds and grasses as well as crops) are destroyed. However, it is not critical to the practice of the present invention that complete destruction of the unwanted plant systems be obtained and it may be sufficient in particular instances if the growth of the plant is merely inhibited.

As representative of the broadleaf weeds and grasses which can be controlled or destroyed in accordance with the present invention, there may be mentioned as illustrative examples: pigweed (*Amaranthus retroflexus*), velvetleaf (*Abutilon theophrasti*), mustard (*Brassica kaber*), and grasses including red millet (*Panicum miliaceum*), green foxtail (*Setaria viridis*), Japanese millet (*Echinochloa crus-galli frumentacea*) and the like.

The active compounds according to the instant invention may be utilized, if desired or necessary, in the form of acceptable formulations or compositions containing liquid or solid inert pesticidal carriers or adjuvants in addition to the active herbicidal agent to provide solutions, emulsions, suspensions, dusts, etc. which facilitate the use and application of the herbicidal agents to a pre-selected substrate. The aforesaid compositions and formulations may be prepared in a known manner, for instance, by admixing the active triazinyl compound of the invention with dispersible liquid diluents and carriers optionally in combination with other vehicles, such as surface-active agents, including emulsifying agents or dispersing agents and suitable solubilizing or diluting solvents. As suitable carriers or vehicles there may be mentioned aromatic hydrocarbons (e.g. benzene, toluene, xylene, etc.) halogenated aromatic hydrocarbons (e.g. chlorobenzenes), paraffins (e.g. petroleum fractions), chlorinated aliphatic hydrocarbons (e.g. methylene chloride, etc.), alcohols (e.g. methanol, ethanol, propanol, butanol, etc.), ethers and ether alcohols (e.g. glycol monomethyl ether, etc.), amines (e.g. ethanolamine, etc.), amides (e.g. dimethylformamide, etc.), ketones (e.g., acetone, etc.), water as well as other conventional solvents. Moreover, solid inert carriers such as kaolins, alumina, silica, calcium carbonate, talc or kieselguhr may be employed. Appropriate nonionic and anionic emulsifying agents or surface active agents, such as polyethylene oxide esters of fatty acids and fatty alcohols, alkyl sulfonates and aryl sulfonates may be used in conjunction with the aforesaid carriers, vehicles, adjuvants and solvents.

The herbicidal compositions in accordance with the present invention may also contain other compatible growth regulants, fungicides, nematocides, insecticides, fertilizers and other known herbicides such as alachlor, atrazine, butylate and simazine. According to the accepted practices in the herbicidal formulating art, when combined with other active herbicidal agents or with carriers, vehicles and the like, the herbicidal compositions of the invention contain from about 0.01 percent to about 99 percent by weight of the instant bis-triazinyls as the active herbicidal component thereof.

The following non-limiting examples are afforded in order that those skilled in the art may more readily understand the present invention and specific preferred embodiments thereof.

EXAMPLE 1

Preparation of 3-Methylthio 1,2,4-Triazine From S-Methylthio Semicarbazide Hydrogen Iodide Into a 1,000 ml. flask equipped with a magnetic stirrer, heat mantle, dropping funnel and condenser are placed 500 ml. of absolute ethanol and 91.2g (1.0 m) of thiosemicarbazide. After heating to 40° C., 142.0g (1.0 m) of methyl iodide is added from the dropping funnel in small divided portions. The contents are heated at reflux for about 1.5 hours and cooled with the precipitated material being filtered off and air dried.

After carrying out three additional runs, the resultant precipitates are combined and dried to obtain 839.5g (90.0% yield) of S-methylthiosemicarbazide hydrogen iodide.

1.0 m of the S-methylthiosemicarbazide hydrogen iodide thus obtained is placed into a 3,000 ml. flask equipped with a magnetic stirrer, thermometer and cooling bath along with 600 ml. of ice-cold water. The temperature is maintained at 5° C. and then 70g (0.48 m) of 40% aqueous glyoxal is added to the flask. 37g (0.44 m) of sodium bicarbonate is dissolved in 1,000 ml. of ice-cold water and added to the flask and the contents are allowed to stir for approximately 15 minutes.

Three additional runs are carried out in the same manner and the contents of each flask extracted eight times with 150 ml. portions of $CHCl_3$, and the combined extracts are dried and evaporated under vacuum. The resultant oily material is extracted with hexane and the material from the four runs is combined to obtain 150 g (73.7% yield) of 3-methylthio-1,2,4-triazine, m.p. 33°–34° C.

EXAMPLE 2

Preparation of 3-Methoxy-1,2,4-Triazine and 3,3'-Dimethoxy-5,5'-bis-1,2,4-Triazinyl Following the procedure outlined in J. Heterocyclic Chem., Vol. 7, pg. 767–771 (1970), 3-methoxy-1,2,4-triazine is prepared as follows.

A solution of 3-methylthio-1,2,4-triazine (25.4 g., 0.2 mole) and 0.22 mole of sodium methoxide in 350 ml. of absolute methanol is stirred at room temperature for twelve hours. Dry-ice is then added to the solution and the precipitated inorganic material removed by filtration. The filtrate is evaporated to dryness and the residue sublimed at 35°/0.3 mm to yield 17.6 g. (79%) of 3-methoxy-1,2,4-triazine. The remaining residue is sublimed at 100° (0.3 mm) to afford 0.8 g. of a yellow solid (m.p. 175°–176.5°, mass spec. mol. wt. 220).

Analysis: Calcd. for $C_8H_8N_6O_2$ (percent): C, 43.63; H, 3.66; N, 38.18. Found: C, 43.34; H, 3.57; N, 37.91.

This compound is identified as 3,3'-dimethoxy-5,5'-bis-1,2,4-triazinyl by its pmr spectrum and conversion to 5,5'-bis-1,2,4-triazinyl.

EXAMPLE 3

Preparation of 3,3'-Dimethoxy-5,5'-bis-1,2,4-Triazinyl

3-Methylthio-1,2,4-triazine (5.08 g., 0.04 mole) is dissolved in ice-cold absolute methanol. To this solution is added 1.2 g. of sodium metal in two portions during a 30 minute interval. The mixture is allowed to stand at room temperature for 16 hours, saturated with Dry-ice and filtered. The solid is washed with 200 ml. of methanol and the washings combined with the filtrate. The combined solution is evaporated to dryness and the residue extracted with chloroform. The chloroform extract, after evaporation to dryness, afforded a yellow solid which is recrystallized from methanol to afford 2.8 g. (63.6%) of 2,2'-dimethoxy-bis-1,2,4-triazinyl, m.p. 175°–176.5°.

EXAMPLE 4

Preparation of 3,3'-Dimethoxy-5,5'-bis-1,2,4-Triazinyl (Potassium Cyanide Catalyzed Coupling)

Following the general procedure outlined in Krass et al, J. Heterocyclic Chem., Vol. 10, p. 345, the above compound is prepared as follows.

A solution of 200 mg. of 3-methoxy-1,2,4-triazine in 15 ml. of water is stirred and heated on a steam bath until complete dissolution of the solid. To the warm solution thus obtained (40° C.) is added an excess of KCN as a solid (500 mg.). An intensely colored precipitate is formed. The solution is stirred with 250 ml. of ethyl ether for 15 minutes and the organic layer separated and dried over anhydrous sodium sulfate. The ether is then evaporated in vacuo to yield the coupled product 3,3'-dimethoxy-5,5'-bis-1,2,4-triazinyl (93% yield).

Analysis: Calcd. for $C_8H_8N_6O_2$ (percent): C, 43.63; H, 3.66; N, 38.13. Found: C, 43.34; H, 3.57; N, 37.91.

EXAMPLE 5

Preparation of 3,3'-Diethoxy-5,5'-bis-1,2,4-Triazinyl

Sodium (30.8g – 1.34g.atm) is reacted with 6 pints of absolute ethyl alcohol below 43° C. 3- Methylthio-1,2,4-triazine (159 g. – 1.25 m) is added, and the black mixture stirred under nitrogen at 40° to 44° C. for 34 minutes. The heating bath is replaced by ice water and carbon dioxide gas bubbled in, giving a red-orange mixture at pH 9 within 2¾ hours. Water (1.25 m) is added and carbon dioxide addition continued for 35 minutes without visible or pH change. Air is introduced for another half hour, giving a brown mixture. One liter of benzene is added and the contents filtered with suction at 19° C. The solids are slurried in a liter of water and extracted with $CHCl_3$ several times. The combined filtrate and extracts are vacuum distilled, giving 3-ethoxy-1,2,4-triazine, b.p. 113°–115° C. at 16 mm. The pot residue is recrystallized from methanol to give 16 g. of golden brown platelets, m.p. 95°–99° C. Recrystallizing again from methanol, and finally from ethyl alcohol, yields 7.7 g. of 3,3'-diethoxy-5,5'-bis-1,2,4-triazinyl.

Analysis: Calcd. for $C_{10}H_{12}N_6O_2$ (percent): C, 48.28, H, 4.87; N, 3385. Found: C, 47.58; H, 4.93; N, 33.39.

EXAMPLE 6

Preparation of 3,3'-Dibutoxy-5,5-bis-1,2,4-Triazinyl

Sodium metal (25.3 g – 1.1 g. atm) is reacted with 3715 ml. n-butanol at 22° to 57° C, then cooled to 38° C. 3-Methylthio-1,2,4-triazine (127 g. – 1.0 m) is added under nitrogen, giving a black solution. Stirring is continued at 38°–43° C. for 80 minutes, then a cooling bath is applied and addition of $CO_2$ commenced. In about 40 minutes at 11° C. the mixture becomes red-orange and its pH is reduced to about 8. Adding air to the $CO_2$ stream during 2 more hours changes the color to orange-yellow at pH of about 9. Following filtration and rinsing with $CHCl_3$, the combined filtrate and rinses are vacuum distilled to yield the monomeric triazine as the major product. The distillation residue is taken up in $CHCl_3$, filtered and evaporated to a black oily residue which is recrystallized from methanol twice to yield 6.7 g of the subject compound and 0.2 g of additional compound from the mother liquor.

Analysis: Calcd. for $CL_4H_{20}N_6O_2$ (percent): 55.25; H, 6.62; N, 27.6. Found: C, 54.65; H, 6.51; N, 28.15.

EXAMPLE 6A

Preparation of 3,3'-Di-n-propoxy-5,5'-bis-1,2,4-Triazinyl

Sodium (30.7 g. – 1.34 g atm) is reacted with 2048 g. n-propyl alcohol near 40° C. 3-Methylthio-1,2,4-triazine (159 g. – 1.25 m) is added, and the mixture stirred under nitrogen at approximately 40° C. for 45 minutes. The mixture is then cooled to 15° C. and saturated with carbon dioxide and air. The black mixture turns orange and the pH is reduced to about 8.5, while producing solids. The mixture is diluted with 1 l. of benzene and filtered with suction. The greasy solids are largely redissolved by stirring with 1300 ml. water and 500 ml. $CHCl_3$. The $CHCl_3$ layer is separated and the aqueous fraction extracted two more times with smaller portions of $CHCl_3$. The combined filtrate and $CHCl_3$ extracts are vacuum distilled to yield the monomeric triazine. The distillation residue is recrystallized from methanol twice to give 9.3 g. of the subject n-propoxy compound (M.P. 104°–106° C), and 6.2 g. of less pure material.

Analysis: Calcd. for $C_{12}H_{16}N_6O_2$ (percent): C, 52.16; H, 5.84; N, 30.42. Found: C, 51.45; H, 5.74; N, 31.35.

EXAMPLE 7

Preparation of 5,5'-bis-1,2,4-Triazinyl

A solution of 6 g. (0.027 mole) of 3,3'-dimethoxy-5,5'-bis-1,2,4-triazine is diluted with 100 ml. of ethanol and 4 g. of 95% aqueous hydrazine added. The resulting solution is refluxed for 24 hours and the precipitated product is filtered from the cooled reaction mixture. The material (5.9 g) is dissolved in 100 ml. of absolute ethanol and 18 g. of yellow mercuric oxide added. The suspension is then heated under reflux for 5.5 hours, cooled, and the ethanol removed by filtration. The solid residue thus obtained is sublimed at 150° C (0.5 mm) to afford 1.4 g. of a yellow solid.

This compound is purified by recrystallization from ethanol to afford, 5,5'-bis-1,2,4-triazinyl (m.p. 210°–212°).

Analysis: Calcd. for $C_6H_4N_6$ (percent): C, 44.99; H, 2.51; N, 52.49. Found: C, 44.77; H, 2.31; N, 51.87. Mass Spec. mol. wt. 160.

EXAMPLE 8

Preparation of 3-Methoxy-3'-Methylthio-5,5'-bis-1,2,4-Triazinyl

Sodium (3.89) is dissolved in 500 ml of absolute methanol. 3,3'-Dimethylthio-5,5'-bis-1,2,4-triazinyl (35.4g) is dissolved in 500 ml of absolute methanol. The methoxide solution is added dropwise to the solution of the triazine. The reaction mixture turns dark green and is stirred overnight. The solution turns orange-yellow when oxygen is bubbled in. Filtration of the resulting orange-yellow solid affords 27.2 g. of the stated product (77% yield).

EXAMPLE 9

Preparation of 3,3'-Diazido-5,5'-bis-1,2,4-Triazinyl 3,3'-Dihydrazino-5,5'-bis-1,2,4-triazinyl (220 mg.–1 mm.) is suspended in 6 ml of 6N HCl. The solution is cooled to 0° C and sodium nitrite (140 mg.–2 meq.) dissolved in 1 ml of water is added dropwise to the solution containing the hydrazino compound while maintaining a temperature of 0°–5° C. The solution is stirred for an additional ½ hour and filtration affords 200 mg. of crude product (80.3% yield). Recrystallization from 95% ethanol affords yellow platlets (m.p. 234° C explosively).

The following additional examples further illustrate the herbicidal utility of the compounds in accordance with the present invention.

EXAMPLES 10–19

Greenhouse Pre-emergent and Post-emergent Herbicide Tests

To illustrate the pre-emergent herbicidal efficacy of the 5,5'-bis-1,2,4-triazine compounds of the present invention, test formulations of representative compounds are prepared by mixing 20 ml. of an acetone solution containing 0.0416g. of the test compound with 20 ml. of water containing 2 ml. of Triton X-155 surfactant. The resultant formulations contain 1040 ppm of test compound, 50% by volume of acetone and 0.025% by volume of surfactant. Appropriate lower concentrations are obtained by diluting this formulation with surfactant-acetone solution so that the concentration of adjuvants is maintained at the original levels.

Seeds of three broadleaf and three grass species are planted in the soil contained in 10 × 8 × 3 inch aluminum pans filled with 1.5 inches of composted soil. The broadleaf species are pigweed, velvetleaf, and mustard; the grasses are red millet, green foxtail and Japanese millet. The pans are then sprayed so that the soil surface is uniformly covered with dilutions of the stock formulation providing dosage rates of the test compounds corresponding to 8, 4, 2, 1, 0.5, 0.25, 0.125, 0.62, etc. lb/A. Two weeks after treatment, percent control (plant kill) at each dosage rate is estimated.

The post-emergent herbicide tests are carried out in the same manner described above, except that the herbicide formulations are applied to the foliage of the seedling plants.

In Table I below, the results obtained according to the foregoing test procedures with respect to the application or dosage rate of the active compounds according to the present invention and the percent weed control (effectiveness) exerted by the test compounds are summarized. Also, where applicable, the specific nature of the herbicidal effect observed is noted.

TABLE I

| Example No. | Test Compound | lbs/A | % CONTROL PREEMERGENT AND POSTEMERGENT |||||| |||||
|---|---|---|---|---|---|---|---|---|---|---|---|---|---|
| | | | Preemergent |||||| Post Emergent |||||
| | | | PW | V | Mu | R | F | J | PW | V | Mu | R | F | J |
| 10 | 3,3'-dimethoxy-5,5'-bis-1,2,4-triazinyl | 8 | 100 | 100 | 100 | 100 | 100 | 100 | 100 | 100 | 100 | 100 | 100 | 100 |
| | | 4 | 100 | 100 | 100 | 100 | 100 | 98 | 100 | 100 | 100 | 100 | 100 | 100 |
| | | 2 | 100 | 98chl | 100 | 98chl | 98chl | 90chl | 100 | 100 | 100 | 100 | 100 | 100 |
| | | 1 | 98 | 95chl | 98chl | 98 | 100 | 90chl | 100 | 100 | 100 | 100 | 100 | 100 |
| | | 0.5 | 30chl | 20chl | 30chl | 0 | 85 | 30 | 100 | 98 | 98 | 100 | 100 | 100 |
| | | 0.25 | 30chl | 20chl | 20 | — | 30chl | 20 | 100 | 95chl | 98 | 100 | 100 | 100 |
| | | 0.125 | 30 | 20chl | 20 | — | 20chl | 0 | 100 | 98chl | 100 | 100 | 100 | 98chl |
| | | 0.062 | 0 | 0 | 0 | — | 0 | — | 90 | 98 | 98 | 98 | 100 | 90 |

TABLE I-continued
% CONTROL PREEMERGENT AND POSTEMERGENT

| Example No. | Test Compound | lbs/A | Preemergent PW | V | Mu | R | F | J | Post Emergent PW | V | Mu | R | F | J |
|---|---|---|---|---|---|---|---|---|---|---|---|---|---|---|
| | | 0.031 | — | — | — | — | — | — | 85 | 90 | 80 | 98 | 98 | 80 |
| | | 0.015 | — | — | — | — | — | — | 80 | 25 | 10 | 10 | 10 | 20 |
| 11 | 3,3'-diethoxy-5,5-bis-1,2,4-triazinyl | 8 | 100 | 100 | 100 | 100 | 100 | 100 | 100 | 100 | 100 | 100 | 100 | 100 |
| | | 4 | 100 | 98 | 100 98 Fechl S9 | 98 chl S9 | 98 Fechl S9 | 100 | 100 | 100 | 100 | 100 | 100 | 100 |
| | | 2 | 98 | 80 | 100 | 98chlS9 | 98 | 95chl | 100 | 100 | 100 | 100 | 100 | 100 |
| | | 1 | 85 | 30 | 60 | 98chl | 95chl | 90 | 100 | 100 | 100 | 100 | 100 | 100 |
| | | 0.5 | 0 | 0 | 20 | 30 | 50 | 30 | 100 | 100 | 100 | 100 | 100 | 100 |
| | | 0.25 | — | — | 20 | 25 | 30 | 25 | 100 | 100 | 100 | 100 | 100 | 100 |
| | | 0.125 | — | — | 0 | 0 | 0 | 0 | 98 | 98 | 90 | 100 | 100 | 95 |
| | | 0.062 | — | — | — | — | — | — | 80 | 35 | 20 | 95 | 80 | 20 |
| | | 0.031 | — | — | — | — | — | — | 80 | 30 | 0 | 95 | 80 | 20 |
| | | 0.015 | — | — | — | — | — | — | 50 | 0 | 10 | 10 | 10 | 10 |
| 12 | 3,3'-dimethythio-5,5'-bis-1,2,4-triazinyl | 8 | 100 30 | 60chl | 100 | 100 | 30* | 100 | 100 | 100 | 100 | 100 | 100 | |
| | | 4 | 100 | 30 | 85 | 100 | 100 | 95chl | 100 | 100 | 100 | 100 | 100 | 100 |
| | | 2 | 85 | 0 | 20 | 98chl | 98chl | 80chl | 100 | 100 | 100 | 100 | 100 | 100 |
| | | 1 | 50 | — | 0 | 98chl | 98chl | 80chl | 100 | 100 | 100 | 100 | 100 | 100 |
| | | 0.5 | 0 | 0 | 0 | 25 | 15 | 0 | 100 | 100 | 100 | 100 | 100 | 100 |
| | | 0.25 | — | — | — | 0 | 0 | — | 98 | 90 | 98 | 100 | 100 | 95 |
| | | 0.125 | — | — | — | — | — | — | 50 | 10 | 10 | 100 | 100 | 50 |
| | | 0.062 | — | — | — | — | — | — | 50 | 10 | 10 | 100 | 100 | 50 |
| | | 0.031 | — | — | — | — | — | — | 50 | 0 | 0 | 100 | 98 | 40 |
| | | 0.015 | — | — | — | — | — | — | 80* | 0 | 0 | 10 | 0 | 0 |
| 13 | 3,3'-dimethyl-5,5'-bis-1,2,4-triazinyl | 8 | 100 | 100 | 100 | 100 | 100 | 100 | 100 | 100 | 100 | 100 | 100 | 100 |
| | | 4 | 100 | 98 | 100 | 100 98 | 100 | 98chl | 100 | 100 | 100 | 100 | 100 | 100 |
| | | 2 | 100 | 98 | 98chl | chl 98 | 98chl | 95chl | 100 | 100 | 100 | 100 | 100 | 100 |
| | | 1 | 100 | 95 | 98 | chl | 99chl | 85 | 100 | 100 | 100 | 100 | 100 | 100 |
| | | 0.5 | 20 | 20 | 20 | 40 | 50 | 60 | 100 | 100 | 100 | 100 | 100 | 100 |
| | | 0.25 | 20 | 20 | 20 | 30 | 0 | 0 | 100 | 100 | 100 | 100 | 100 | 100 |
| | | 0.125 | 0 | 0 | 0 | 0 | 0 | 0 | 100 | 100 | 90 | 100 | 100 | 90 |
| | | 0.062 | — | — | — | — | — | — | — | — | — | — | — | — |
| | | 0.031 | — | — | — | — | — | — | 85 | 95 | 25 | 99 | 95 | 60 |
| | | 0.015 | — | — | — | — | — | — | 80 | 30 | 10 | 30 | 20 | 30 |
| 14 | 5,5'-bis-1,2,4-triazinyl | 8 | 100 | 100 | 100 | 100 | 100 | 100 | 100 | 100 | 100 | 100 | 100 | 100 |
| | | 4 | 100 | 30 | 100 | 95chl | 95 | 90$^{Fe}$ | 100 | 100 | 100 | 100 | 100 | 100 |
| | | 2 | 95 | 0 | 98 | 20 | 20$^{Fe}$ | 80$^{Fe}$ | 100 | 85 | 100 | 100 | 95 | 85 |
| | | 1 | 30 | 0 | 30 | 20 | 0 | 80$^{Fe}$ | 100 | 20 | 100 | 95 | 95 | 80 |
| | | 0.5 | 0 | — | 0 | 20 | — | 40$^{Fe}$ | 95 | 20 | 80 | 90 | 80 | 20 |
| | | 0.25 | — | — | — | — | — | 20$^{Fe}$ | 30 | 20 | 50 | 0 | 30 | 50 |
| | | 0.125 | — | — | — | — | — | — | — | — | — | — | — | — |
| 15 | 3,3'-diazido-5,5'-1,2,4-triazinyl | 8 | 100 | 100 | 100 | 100 | 100 | 100 | 100 | 100 | 100 | 100 | 100 | 100 |
| | | 4 | — | — | — | — | — | — | — | — | — | — | — | — |
| | | 2 | 100 | 100 | 100 | 100 | 100 | 40 | 100 | 100 | 100 | 100 | 100 | 100 |
| | | 1 | 98 | 80 | 50 | 10 | 10 | 10 | 100 | 100 | 100 | 100 | 100 | 95 |
| | | 0.5 | 50 | 0 | 0 | 0 | 0 | 0 | 100 | 100 | 100 | 100 | 100 | 90 |
| | | 0.25 | 0 | — | — | — | — | — | 100 | 80 | 100 | 100 | 100 | 90 |
| | | 0.125 | — | — | — | — | — | — | 98 | 30 | 80 | 50 | 50 | 30 |
| 16 | 3-methoxy-3'-methylthio-5,5'-bis-1,2,4-triazinyl | 8 | 100 | 100 | 100 | 100 | 100 | 100 | 100 | 100 | 100 | 100 | 100 | 100 |
| | | 4 | 100 | 100 | 100 | 100 | 100 | 100 | 100 | 100 | 100 | 100 | 100 | 100 |
| | | 2 | 30 | 0 | 60 | 50chl | 100 | 90chl | 100 | 100 | 100 | 100 | 100 | 100 |
| | | 1 | 0 | — | 60 | 30chl | 100 | 90chl | 100 | 100 | 100 | 100 | 100 | 100 |
| | | 0.5 | 0 | 0 | 0 | 0 | 50 | 60 | 100 | 100 | 100 | 100 | 100 | 100 |
| | | 0.25 | 0 | 0 | 0 | 0 | 50 | 0 | 100 | 100 | 100 | 100 | 100 | 100 |
| | | 0.125 | 0 | 0 | 0 | 0 | 50 | 0 | 100 | 90 | 95 | 100 | 100 | 100 |
| | | 0.062 | 0 | 0 | 0 | 0 | 0 | 0 | 0* | 30 | 90 | 100 | 100 | 50 |
| | | 0.031 | — | — | — | — | — | — | — | — | — | — | — | — |
| 17 | 1,1'-N-oxide-3,3'-dimethoxy-5,5'-bis-1,2,4-triazinyl | 8 | 100 | 100 | 100 | 100 | 100 | 98 | 100 | 100 | 100 | 100 | 100 | 100 |
| | | 4 | 98 | 100 | 90 | 85chl | 10* | 100 | 100 | 100 | 100 | 100 | 100 | 100 |
| | | 2 | 98 | 40 | 0 | 80chl | 85chl | 0 | 100 | 100 | 100 | 100 | 100 | 100 |
| | | 1 | 30 | 40 | 0 | 50chl | 85chl | 0 | 100 | 100 | 100 | 100 | 100 | 100 |
| | | 0.5 | 0 | 20 | 0 | 20 | 0 | — | 100 | 100 | 100 | 100 | 100 | 90 |
| | | 0.25 | — | 0 | — | — | 0 | — | 0 | 40Fe | 0 | 0 | 0 | 0 |
| 18 | 3,3'-diethyl-5,5'-bis-1,2,4-Triazinyl | 8 | 100 | 100 | 100 | 100 | 100 | 100 | 100 | 100 | 100 | 100 | 100 | 100 |
| | | 4 | 100 | 100 | 100 | 100 | 100 | 100 | 100 | 100 | 100 | 100 | 100 | 100 |
| | | 2 | 100 | 100 | 100 | 100 | 100 | 100 | 100 | 100 | 100 | 100 | 100 | 100 |
| | | 1 | 100 | 95 | 100 | 100 | 100 | 90 | 100 | 100 | 100 | 100 | 100 | 100 |
| | | 0.5 | 98 | 30 | 100 | 50 | 90 | 85 | 100 | 90 | 100 | 100 | 100 | 100 |
| | | 0.25 | 0 | 0 | 50 | 30 | 80 | 50 | 100 | 90 | 98 | 100 | 100 | 100 |
| | | 0.125 | — | — | 0 | 0 | 0 | 20 | 60 | 30 | 95 | 100 | 100 | 80 |
| | | 0.062 | — | — | — | — | — | 0 | 0 | 0 | 30 | 75 | 80 | 50 |
| | | 0.031 | — | — | — | — | — | — | — | — | 0 | 0 | 0 | 0 |
| 19 | 5,5'-diphenyl-3,3'-bis-1,2,4-triazinyl (comparative test compound of Example 5, U.S. | 8 | 0 | 0 | 0 | 0 | 0 | 0 | 0 | 0 | 0 | 0 | 0 | 0 |
| | | 4 | 0 | 0 | 0 | 0 | 0 | 0 | 0 | 0 | 0 | 0 | 0 | 0 |
| | | 2 | 0 | 0 | 0 | 0 | 0 | 0 | 0 | 0 | 0 | 0 | 0 | 0 |
| | | 1 | 0 | 0 | 0 | 0 | 0 | 0 | 0 | 0 | 0 | 0 | 0 | 0 |

TABLE I-continued

| Example No. | Test Compound | lbs/A | % CONTROL PREEMERGENT AND POSTEMERGENT | | | | | | | | | | | |
|---|---|---|---|---|---|---|---|---|---|---|---|---|---|---|
| | | | Preemergent | | | | | | Post Emergent | | | | | |
| | | | PW | V | Mu | R | F | J | PW | V | Mu | R | F | J |
| | Patent No. 3,498,981) | 0.5 | 0 | 0 | 0 | 0 | 0 | 0 | 0 | 0 | 0 | 0 | 0 | 0 |
| | | 0.25 | 0 | 0 | 0 | 0 | 0 | 0 | 0 | 0 | 0 | 0 | 0 | 0 |
| | | 0.125 | 0 | 0 | 0 | 0 | 0 | 0 | 0 | 0 | 0 | 0 | 0 | 0 |
| | | 0.062 | 0 | 0 | 0 | 0 | 0 | 0 | 0 | 0 | 0 | 0 | 0 | 0 |
| | | 0.031 | 0 | 0 | 0 | 0 | 0 | 0 | 0 | 0 | 0 | 0 | 0 | 0 |
| | | 0.015 | 0 | 0 | 0 | 0 | 0 | 0 | 0 | 0 | 0 | 0 | 0 | 0 |

Note:*Observed effect does not correlate with remainder of data.
- Dashes indicate absence of testing at stated application rate.
Pw = pigweed
V = velvetleaf
Mu = mustard
R = red millet grass
F = green foxtail
J = Japanese millet
Fe =0 formative effect
chl = chlorosis
S = stunting, from 1 (slight) to 9 (severe)

Field Test — Crop Selectivity

In order to evaluate the relative crop selectivity of two of the active herbicides of the present invention at various dosage rates, test plots (30 square feet) of fertilized, light sandy soil containing approximately 1% organic matter are seeded with crop plants. The test herbicides are applied as a direct or broadcast spray to plants at a pre-selected crop stage and compared with the results obtained with atrazine. An injury rating (expressed as a percent) is assigned to each of the crops with zero denoting no injury to the plant and 100 indicating complete destruction thereof. The herbicides, crops, application rates and results are summarized in Table II below.

TABLE II

| CROP | METHOD OF APPLICATION | TEST COMPOUND RATE (lb/A) | CROP INJURY (%) COMPOUND OF EXAMPLE 10 | | | | COMPOUND OF EXAMPLE 13 | | | | ATRAZINE | | | |
|---|---|---|---|---|---|---|---|---|---|---|---|---|---|---|
| | | | ⅛ | ¼ | ½ | 1 | ⅛ | ¼ | ½ | 1 | ⅛ | ¼ | ½ | 1 |
| Soybean | ot* | | 43 | 57 | 73 | 89 | 37 | 57 | 73 | 99 | 43 | 70 | 99 | 100 |
| Soybean | dir** | | 13 | 37 | 53 | 77 | 35 | 50 | 73 | 90 | 35 | 70 | 93 | 100 |
| Corn,sweet | ot | | 43 | 67 | 80 | 96 | 27 | 37 | 60 | 82 | 0 | 0 | 0 | 10 |
| Cotton | ot | | 97 | 100 | 100 | 100 | 38 | 73 | 90 | 97 | 90 | 100 | 100 | 100 |
| Cotton | dir | | 68 | 83 | 96 | 100 | 8 | 23 | 37 | 67 | 47 | 87 | 100 | 100 |
| Peanut | ot | | — | 40 | 57 | 88 | — | 23 | 67 | 77 | — | 50 | 75 | 90 |
| Sorghum | ot | | — | 33 | 93 | 100 | — | 10 | 23 | 57 | — | 0 | 0 | 10 |
| Sorghum | dir | | 0 | 0 | 13 | 30 | 0 | 0 | 13 | 30 | 0 | 0 | 0 | 15 |
| Onion | ot | | 3 | 13 | 40 | 93 | 0 | 20 | 70 | 100 | 67 | 100 | 100 | 100 |
| Wheat | ot | | 2 | 13 | 37 | 70 | 0 | 10 | 50 | 95 | 27 | 90 | 100 | 100 |
| Oat | ot | | 3 | 20 | 47 | 77 | 10 | 20 | 60 | 95 | 43 | 94 | 100 | 100 |
| Tomato | ot | | 92 | 96 | 100 | 100 | 40 | 80 | 100 | 100 | 100 | 100 | 100 | 100 |
| Cabbage | ot | | 100 | 100 | 100 | 100 | 100 | 100 | 100 | 100 | 100 | 100 | 100 | 100 |
| Cucumber | ot | | 85 | 100 | 100 | 100 | 70 | 100 | 100 | 100 | 100 | 100 | 100 | 100 |
| Lettuce, leaf | ot | | 93 | 98 | 98 | — | — | — | — | — | 97 | 100 | 100 | — |
| Radish | ot | | 40 | 60 | 77 | — | — | — | — | — | 45 | 65 | 75 | — |
| Carrot | ot | 30 | 72 | 92 | — | — | — | — | — | 30 | 72 | 92 | — | — |
| Rice | ot | | 40 | 60 | 67 | — | — | — | — | — | 40 | 60 | 67 | — |

*ot = over-the-top of crops (broadcast)
dashes indicate not tested
**dir = applied to plant stem As is evident from the foregoing results, certain of the compounds of the invention are effective at relatively low dosage rates both pre- and post-emergence for the control of broadleaf and grassy-type weeds. Moreover, certain of the compounds, e.g., the 3,3'-dimethoxy and 3,3'-dimethyl-5,5'-bis-1,2,4-triazinyl compounds, evidence a high degree of crop selectivity (low injury rate), particularly with respect to grain sorghum, onion, wheat and oats at dosage rates ranging from between about 0.125 to 0.25 lb/A.

As indicated by the test data presented hereinabove, one of the distinct advantages of the herbicidally active compounds of the present invention is the relatively low dosage rate (and, therefore reduced cost of weed control) required for acceptable control of broadleaf and grassy-type weed species.

While the invention has been described and illustrated with reference to certain preferred embodiments thereof, those skilled in the art will appreciate that various changes, modifications and substitutions can be made therein without departing from the spirit of the invention. For instance, dosage rates other than the preferred ranges set forth hereinabove may be applicable as a consequence of variations in soils with respect to permeability, natural plant productivity, prior chemical treatment, etc. as well as difference in environmental conditions including light, moisture, temperature, wind and the like. Likewise, the specific results observed with respect to weed control and crop selectivity may vary depending on whether the active herbicides of the present invention are used alone or in combination with each other or other known herbicidal agents as well as the specific type of formulation employed in applying the herbicidal agents to the plant systems and such expected variations in results are contemplated in accordance with the objects and practices of the present invention. It is intended, therefore, that the invention be limited only by the scope of the claims which follow.

What is claimed is:

1. A method for controlling undesired plant life which comprises applying to the situs thereof a herbicidally effective amount of at least one active compound of the formula:

wherein R and R' are the same or different and represent hydrogen, $C_1$–$C_6$ alkyl, $C_1$–$C_6$ alkoxy, $C_1$–$C_4$ alkylthio, $C_1$–$C_4$ alkylamino, di-($C_1$–$C_4$-alkyl) amino, $C_1$–$C_4$ alkylsulfonyl, azido, or a group —OA wherein A is a cation, R" and R'" are the same or different and represent hydrogen or $C_1$–$C_4$ alkyl, the alkyl moieties of said R, R', R" and R'" being branched or straight chain and the N-oxide derivatives thereof.

2. The method as defined in claim 1, wherein said active compound is applied pre-emergence to control undesired plant life.

3. The method as defined in claim 1, wherein said active compound is applied post-emergence to control undesired plant life.

4. The method as defined in claim 3, wherein said herbicidally effective amount of said active compound ranges between about 0.015 to about 8 lb/A.

5. The method as defined in claim 3, wherein said herbicidally effective amount of said active compound ranges between about 0.031 to 0.5 lb/A.

6. The method as defined in claim 3, wherein said herbicidally effective amount of said active compound ranges between about 0.062 to 0.25 lb/A.

7. The method as defined in claim 1, wherein said undesired plant life comprises broadleaf or grassy-type weeds and said active compound is applied post-emergence for the control thereof.

8. The method as defined in claim 7 wherein said active compound is applied in the presence of a desired crop and in an amount sufficient to promote a selective herbicidal effect.

9. The method as defined in claim 1 wherein said active compound is selected from the group consisting of 5,5'-bis-1,2,4-triazinyl, 3,3'-dimethylthio-5,5'-bis-1,2,4-triazinyl, 3,3'-dimethoxy-5,5'-bis-1,2,4-triazinyl, 3,3'-diethoxy-5,5'-bis-1,2,4-triazinyl, 3,3'-dipropoxy-5,5'-bis-1,2,4-triazinyl, 3,3'-dibutoxy-5,5'-bis-1,2,4-triazinyl, 3,3'-dimethyl-5,5'-bis-1,2,4-triazinyl, 3,3'-diethyl-5,5'-bis-1,2,4-triazinyl, 3,3'-dibutyl-5,5'-bis-1,2,4-triazinyl, 3,3'-diazido-5,5'-bis-1,2,4-triazinyl and 3-methylthio-3'-methoxy-5,5'-bis-1,2,4-triazinyl.

10. The method as defined in claim 1, wherein said active compound is 3,3'-dimethoxy-5,5'-bis-1,2,4-triazinyl.

11. A herbicidal composition comprising a herbicidally acceptable carrier substance and a herbicidally effective amount of at least one active compound of the formula:

wherein R and R' are the same or different and represent hydrogen, $C_1$–$C_6$ alkyl, $C_1$–$C_6$ alkoxy, $C_1$–$C_4$ alkylthio, $C_1$–$C_4$ alkylamino, di-($C_1$–$C_4$-alkyl) amino, $C_1$–$C_4$ alkylsulfonyl, azido, or a group —OA wherein A is a cation, R" and R'" are the same or different and represent hydrogen or $C_1$–$C_4$ alkyl, the alkyl moieties of said R, R', R" and R'" being branched or straight chain and the N-oxide derivatives thereof.

12. The composition as defined in claim 11, wherein said herbicidally acceptable carrier substance is selected from the group consisting of liquid carrier vehicles and finely divided solid carriers.

13. The herbicidal composition as defined in claim 11 wherein said active compound comprises between about 0.01% to about 99% by weight relative to the total of said composition.

14. The herbicidal composition as defined in claim 11 wherein said active compound is 3,3'-dimethoxy-5,5'-bis-1,2,4-triazinyl.

15. A method for controlling undesired plant life which comprises applying to the situs thereof a herbicidally effective amount of the composition as defined in claim 11.

16. A compound of the formula:

wherein R and R' are the same and selected from propoxy, butoxy, azido, alkali metal hydroxide, methylamino, dimethylamino or methylsulfonyl; or wherein R and R' are different and independently selected from methylthio and methoxy; or wherein R and R' are the same and selected from dimethylamino or dimethoxy and the 1,1'-hetero nitrogen atoms are substituted by oxygen to form the N-oxides thereof.

17. The compound as defined in claim 16 wherein said compound is 3,3'-dibutoxy-5,5'-bis-1,2,4-triazinyl.

18. The compound as defined in claims 16 wherein said compound is 3,3'-diazido-5,5'-bis-1,2,4-triazinyl.

19. The compound as defined in claim 16 wherein said compound is 3-methoxy-3'-methylthio-5,5'-bis-1,2,4-triazinyl.

20. A method for controlling undesired plant life which comprises applying to the situs thereof at least one of the compounds as defined in claim 16.

21. A herbicidal composition which comprises a herbicidally acceptable carrier substance selected from the group consisting of liquid carrier vehicles and finely divided solid carriers and a herbicidally effective amount of at least one of the compounds as defined in claim 16.

* * * * *